United States Patent [19]

Reuther et al.

[11] 4,104,374
[45] Aug. 1, 1978

[54] WOOD PRESERVATIVE

[75] Inventors: Wolfgang Reuther, Ziegelhausen; Knut Oppenlaender; Paul Raff, both of Ludwigshafen; Ernst-Heinrich Pommer, Limburgerhof; Manfred Siegler, Frankenthal, all of Fed. Rep. of Germany

[73] Assignee: BASF Aktiengesellschaft, Ludwigshafen am Rhein, Fed. Rep. of Germany

[21] Appl. No.: 697,769

[22] Filed: Jun. 21, 1976

[30] Foreign Application Priority Data

May 18, 1976 [DE] Fed. Rep. of Germany ....... 2622028

[51] Int. Cl.$^2$ .............................................. A01N 9/00
[52] U.S. Cl. ................................ 424/185; 260/462 R; 264/109; 428/424; 428/528; 428/529; 428/537
[58] Field of Search .................... 424/185; 260/462 R

[56] References Cited

U.S. PATENT DOCUMENTS

| | | | |
|---|---|---|---|
| 2,260,339 | 10/1941 | Prescott et al. | 260/462 R |
| 2,839,564 | 6/1958 | Garner | 260/462 R |
| 2,894,020 | 7/1959 | McManimie | 260/462 R |
| 2,989,468 | 6/1961 | Darling et al. | 260/462 R |
| 3,009,799 | 11/1961 | Dykstra | 260/462 R |
| 3,325,262 | 6/1967 | De Gray et al. | 424/185 |

FOREIGN PATENT DOCUMENTS 722,538 1/1955 United Kingdom.

*Primary Examiner*—Allen J. Robinson
*Attorney, Agent, or Firm*—Keil, Thompson & Shurtleff

[57] ABSTRACT

Wood preservatives containing a boric acid/alkylene oxide adduct, with alkylene of 2 to 8 carbon atoms, and a process for protecting wood against fungi and insects with this agent.

5 Claims, No Drawings

WOOD PRESERVATIVE

The present invention relates to wood preservatives containing as active ingredient a boric acid/alkylene oxide adduct.

It is known (Chemical Week, July 26, 1972, p. 43) to use boric acid for protecting wood against insects and fungi.

We have found that boric acid/alkylene oxide adducts have a strongly destructive action on wood-destroying insects and fungi, and are therefore eminently suitable as wood preservatives. By "wood" is meant not only solid wood but also wood-base materials prepared from wood particles, e.g., wood chips.

The adducts exhibit not only a good fungicidal action but also an action on ligniperdous insects such as *Hylotrupes bajalus, Anobium punctatum* and *Lyctus brunneus*, and on termites. The following ligniperdous fungi and soft rot and mold fungi may be controlled with the active ingredients of the invention: *Coniophora cerebella, Merulius lacrimans, Lentinus lepideus, Lenzites trabea, Porio vaporaria, Polystictus (Coriolus) versicolor, Paxillus panuoides, Stereum purpureum, Fomes annosus, Bispora effusa, Stachybotrys atra, Chaetomium globosum, Trichoderma viride, Aspergillus niger, Hormiscium spec.*, and *Stemphylium spec.*

By contract to boric acid and borax, which are unsuitable as active ingredients for oil-type wood preservatives on account of their poor solubility in organic solvents, the boric acid/alkylene oxide adducts are very readily soluble in the aromatic and aliphatic solvents usually employed; these active ingredients in solvent formulations also mix well with other fungicides and insecticides used for protecting wood. Compounds with which the adducts of the invention are miscible are for example the aluminum salt of N-cyclohexyl-N-nitrosohydroxylamine, pentachlorophenol, chloronaphthalene, N-dichlorofluoromethylthio-N',N'-dimethyl-N-phenylsulfonyl diamide, and N-phenyl-N,N'-dimethyl-N'-dichlorofluoromethylthiosulfonyl diamide. The active ingredients may not only be used in solvent wood preservative formulations which are applied to the wood by painting, dipping or spraying, but also added, in aqueous solution, to glues for the manufacture of wood-base materials. Suitable binders for the manufacture of wood-base materials are urea/formaldehyde, melamine/formaldehyde, urea/formaldehyde/melamine and isocyanate resins. As the active ingredient solutions can be added to the glue direct, there is no danger, as is the case with boric acid, of the formation of lumps which result in poor distribution of the active ingredient. It is also known that, when boric acid is mixed with wood chips before gluing, difficulties occur with regard to homogeneous distribution. Furthermore, aqueous active ingredient solutions may also be used for impregnating wood by the pressure process.

The wood to be protected against insect and fungus attack is treated with the preservative in such a manner that the active ingredient is uniformly distributed over the surface of the wood and penetrates into the wood as far as possible. When the surface is treated, the application rate is approximately 5 to 100 g of active ingredient per $m^2$. For impregnation, or for the treatment of wood chips in the manufacture of wood-base materials, the application rate is about 5 to 25% of active ingredient, based on dry wood substance. Examples of suitable solvents for the active ingredient are benzene fractions containing up to 30wt% of aromatics, drying oils such as are used in painting, alcohols, esters, ketones and glycol ethers. The active ingredient may also be mixed with solid carriers such as clay, silica gel, lime dust and diatomaceous earth. The active ingredients are manufactured by reacting alkylene oxides of 2 to 8 carbon atoms with o-boric acid in a molar ratio of from 5:1 to 1:1 in the presence of aprotic organic solvents thermally at from 100° to 160° C or in the presence of catalytic amounts of bases or Lewis acids at from 70° to 120° C in a closed system and at pressures of from 4 to 9 bars.

The wood preservatives contain from about 1 to 30wt% of the boric acid/alkylene oxide adduct.

The starting compound is o-boric acid; other starting materials are alkylene oxides of from 2 to 8 carbon atoms. Preferred alkylene oxides are aliphatic, such as ethylene oxide, propylene oxide, 1,2- and 2,3-butylene oxide and isobutylene oxide, and araliphatic, such as styrene oxide. Mixtures of oxides may also be used, in which case a mixture of alkoxylated boric acids is obtained.

In accordance with the invention, "aprotic organic solvents" are those which do not possess a mobile hydrogen atom in the molecule. The may be polar or non-polar. Examples of polar solvents are acetone, dioxane, dimethylformamide, formamide, and dimethyl acetamide; carbon tetrachloride is an example of a non-polar solvent.

The reaction may be carried out at temperatures of from 100° to 160° C, preferably 120° to 150° C, without the addition of catalysts. It is however preferred to carry out the reaction in the presence of bases or Lewis acids becasue these reagents have a catalytic action. Examples of bases are tertiary amines such as dimethyldodecylamine, catalytic amounts of an alkali such as sodium hydroxide, and alkoxides such as sodium methylate and potassium tert-butylate; examples of Lewis acids are boron trifluoride etherate, aluminum chloride and zinc chloride. When catalysts are used, the temperatures employed are from 70° to 120° C, preferably from 80° to 110° C.

In this case the reaction is expediently carried out in a closed system, for instance an autoclave, in which is placed the aprotic solvent and to which is added from 20 to 200wt%, based on solvent, of o-boric acid and, if desired, from 0.1 to 5wt%, of base or Lewis acid, based on o-boric acid.

The system is then pressured, in accordance with the molar ratios given, with from 1 to 5 times, preferably from 3 to 4 times, the molar amount of alkylene oxide, based on o-boric acid, and the contents heated, as stated above, to from 70° to 120° C, preferably from 80° to 110° C. By defintion the pressure should rise to from 4 to 9, preferably 5 to 7, bars. The total duration of the reaction is about 3 to 8, preferably 5 to 6, hours.

Upon completion of the reaction and after the pressure in the reaction vessel has been let down, the solvent and water of reaction are removed by distillation.

Depending on the amount and type of alkylene oxide used, there remain water-soluble to water-insoluble, liquid to viscous products which can be characterized by viscosity, infrared spectroscopy, and mass spectroscopy.

Viscosity measurements carried out on propoxylation products give for instance — at 20° C — viscosities of 1,600 to 1,700 cSt; butoxylation products approx. 100 cSt.

Infrared spectra have B—O bands at 1,310 to 1,350 $cm^{-1}$.

In mass spectroscopy, characteristic fragments are obtained from which it is possible to conclude that the reaction products are, depending on the molar ratios of boric acid to alkylene oxide, cyclic esters, the most frequent of which are compounds having the following structure:

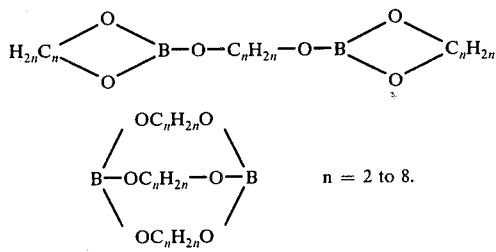

n = 2 to 8.

Some of the products obtained by the process of the invention can be purified by distillation and fractionated. They may be used as a mixture or as individual fractions.

The following examples, in which the parts are by weight, illustrate the invention.

EXAMPLE 1 o-boric acid/1,2-butylene oxide

In a $V_2A$ stirred autoclave are placed 93 parts (1.5 moles) of o-boric acid, 93 parts of dioxane and 2.79 parts (3wt%, based on o-boric acid) of dimethyldodecylamine; subsequently, 432 parts (6 moles) of 1,2-butylene oxide is pressured in in portions at 130° to 140° C.
Pressuring time: 8 hours
Pressure: 7 atmospheres gauge
Temperature: 138° C
Stirring time: 3 hours A clear brown liquid is obtained. The rate of conversion, based on oxide consumption, is 1:3.6.

After removal of residual epoxide and the mixture of dioxane and water of reaction, three fractions are obtained:

| Fraction I: | b.p. (0.7 mm) 57° C, 37 g; | $n_D^{20}$: 1.4390 |
|---|---|---|
| Fraction II: | b.p. (0.5 mm) 120° – 130° C, 75 g; | $n_D^{20}$: 1.4400 – 1.4404 $D^{20}$: 0.995 |
| Fraction III: | b.p. (0.5 mm) 145° – 160° C, 17 g; (290 g of resinous residue) | $n_D^{20}$: 1.4411 – 1.4444 $\eta_{20}$ = 98 cP (98.6 cSt) |

EXAMPLE 2 o-boric acid/ethylene oxide

In a $V_2A$ stirred autoclave are placed 248 parts (4 moles) of o-boric acid, 248 parts of dioxane and 3.72 parts (1.5wt%, based on o-boric acid) of $BF_3$ etherate; subsequently, 528 parts (12 moles) of ethylene oxide is pressured in in portions at 110° to 120° C, and unreacted ethylene oxide and the mixture of dioxane and water of reaction are removed in vacuo at 90° to 100° C/15 mm Hg.

There is obtained 775 parts of a pasty wax-like (Vaseline-like) compound. The rate of conversion, based on oxide consumption, is 1:3.
Pressuring time: 6 hours
Pressure: 7 atmospheres gauge
Temperature: 110°–115° C
Stirring time: 3 hours

EXAMPLE 3 o-boric acid/1,2-butylene oxide

In a $V_2A$ stirred autoclave are placed 93 parts (1.5 moles) of o-boric acid, 186 parts of dioxane and 2.79 parts (3wt%, based on o-boric acid) of sodium methylate; subsequently, 378 parts (5.25 moles) of 1,2-butylene oxide is pressured in in portions at 135° to 140° C.
Pressuring time: 6 hours
Pressure: 7 atmospheres gauge
Temperature: 138° C
Stirring time: 3 hours 11 parts of unreacted o-boric acid is separated by suction filtration from the dioxane solution containing water of reaction. The rate of conversion, based on oxide consumption, is 1:2.5.

After removal of the dioxane-water mixture, the unreacted epoxide and high vacuum distillation, three fractions are obtained:
Fraction I: b.p. (0.1 mm) 53°–55° C/23 parts of a pale yellow oil
Fraction II: b.p. (0.2 mm) 95° C/14 parts of a pale brown oil
Fraction III: b.p. (0.3 mm) 160° C/42 parts of a pale brown oil 90 g of a resinous residue

EXAMPLE 4 o-boric acid/propylene oxide

In a $V_2A$ stirred autoclave are placed 248 parts (4 moles) of o-boric acid, 7.44 parts (3wt%, based on o-boric acid) of dimethyldodecylamine and 248 parts of dioxane; subsequently, 928 parts (16 moles) of propylene oxide is pressured in in portions at from 100° to 110° C.
Pressuring time: 8 hours
Pressure: 8 atmospheres gauge
Temperature: 108° C
Stirring time: 3 hours After removal of the excess propylene oxide and the mixture of dioxane and water of reaction, 1.013 parts of a pale yellow oil is obtained.
$d^{20}$: 1.070–1.065
$n_D^{20}$: 1.444
$\eta_{20}$: 1.695 cP
b.p. (760 mm): 270° C
Rate of conversion, based on oxide consumption: 1:3.3

EXAMPLE 5 o-boric acid/2,3-butylene oxide

In a $V_2A$ stirred autoclave are placed 93 parts (1.5 moles) of o-boric acid, 93 parts of dioxane and 2.79 parts (3wt%, based on o-boric acid) of dimethyldodecylamine; subsequently, 432 parts (6 moles) of 2,3-butylene oxide is pressured in in portions at from 120° to 140° C.
Pressuring time: 8 hours
Pressure: 8 atmospheres gauge
Temperature: 138° C
Stirring time: 3 hours
Rate of conversion, based on oxide consumption: 1:2.35

After removal of residual epoxide and the mixture of dioxane and water of reaction, and after high vacuum distillation, three fractions are obtained as pale yellow to colorless liquids:

| | | | |
|---|---|---|---|
| Fraction I: | b.p. (0.4 mm) 70° C (37 g); | $n_D^{20}$: 1.4324; | $\eta_{20} = 135$ cP (133.5 cSt) |
| Fraction II: | b.p. (0.4 mm) 90° C (22 g); | $n_D^{20}$: 1.4330; | $\eta_{20} = 140$ cP (139.5 cSt) |
| Fraction III: b.p. (0.4 mm) 146° C (95 g); | $n_D^{20}$: 1.4330; | | $\eta_{20} = 145$ cP (143.5 cSt) |
| 89 g of a resinous residue | | | |

EXAMPLE 6 o-boric acid/isobutylene oxide

In a $V_2A$ stirred autoclave are placed 124 parts (2 moles) of o-boric acid, 62 parts of dioxane, and 3.72 parts (3wt%, based on o-boric acid) of sodium methylate; subsequently, 504 parts (7 moles) of isobutylene oxide is pressured in in portions at from 140° to 150° C.
Pressuring time: 9 hours
Pressure: 8 atmospheres gauge
Stirring time: 3 hours After removal of the residual epoxide and the mixture of dioxane and water of reaction at subatmospheric pressure, there is obtained 290 parts of a yellow oil.

Rate of conversion, based on oxide consumption: 1:1.15
Boiling point (0.3 mm): 105° C
$\eta_{20} = 52.4$ cP (= 51 cSt)
$D^{20}$: 1.028
pH: 4.5

EXAMPLE 7 o-boric acid/styrene oxide

In a 2 liter $V_2A$ stirred autoclave are introduced 62 parts (1 mole) of o-boric acid, 62 parts of dioxane, 1.86 parts (3wt%, based on o-boric acid) of dimethyldodecylamine, and 360 parts (3 moles) of styrene oxide; the contents are slowly heated, and stirred for 6 hours at 150° C under a nitrogen blanket.

After removal of the dioxane in vacuo, there is obtained 350 parts of a red-brown, viscous, water-insoluble product.

Rate of conversion, based on oxide consumption: 1:2.4

EXAMPLE 8

To prepare an oil-type wood preservative containing 7.5% of boric acid/propylene oxide product, 7.5 parts of the latter product (Example 4) is mixed with 13.7 parts of an alkyd resin of medium oil content (20% solid resin). There is then added 47.3 parts of an aromatics-containing benzene fraction, the mixture is if desired filtered to remove impurities, and is then made up to 100 parts with a benzene fraction containing aliphatic compounds.

EXAMPLE 9

An oil-type wood preservative containing 15.1% of active ingredient is prepared in similar manner, except that only 39.7 parts of the aromatics-containing benzene fraction is used instead of 47.3 parts.

EXAMPLE 10

To determine the effectiveness of the preservatives of the invention on wood-destroying fungi, pine sapwood and beechwood blocks 50×25×15 mm in size were coated with 200 g/m² of wood surface of the oil-type wood preservative formulations of Examples 8 and 9.

After 4 weeks' storage the treated blocks were placed, together with untreated controls, in glass dishes containing, in a nutrient medium, the test fungi *Coniophora cerebella* and *Polystictus (Coriolus) versicolor*. The dishes were then incubated under controlled conditions (22° C; 70% relative humidity).

After 4 months the mycelium adhering to the blocks was removed and the blocks were dried. The weight loss and degree of wood destruction were then ascertained.

| Amount of boric acid/ propylene oxide product in formulation in % | *Coniophora cerebella* (pinewood) | | *Polystictus versicolor* (beechwood) | |
|---|---|---|---|---|
| | weight loss in % | degree of destruction | weight loss in % | degree of destruction |
| 7.5 | 0 | 1 | 2 | 2a |
| 15.1 | 0 | 1 | 0 | 1 |
| Control (untreated) | 21 | 3b/4a | 18 | 3b |

Scale
1 = undamaged
2a = slight attack in parts
2b = slight attack overall
3a = marked attack in parts
3b = marked attack overall
4a = completely destroyed in parts
4b = completely destroyed overall

EXAMPLE 11

The boric acid/propylene oxide product was added as preservative to an aqueous wood glue mixture based on a urea/formaldehyde polycondensate. Beech and spruce chips were glued with these binder mixtures, 9 parts of resin (dry weight) being used for 100 parts of chips. The chips coated with binder were pressed for 6 minutes at a temperature of 165° C to give 18 mm thick chipboard. The amount of preservative was such that the finished boards contained 7.5% of the boric acid/propylene oxide product, based on dry chips. For comparison purposes, chipboard was produced to which boric acid in powder form had been admixed in amounts of 2%, based on dry chips, after the chips had been glued. The amount of 2% boric acid corresponds to the boric acid content of the 7.5% boric acid propylene oxide product obtained in accordance with Example 4.

Specimens 50×25×18 mm in size were cut from the chipboard and examined as to their resistance to attack by the wood-destroying fungi *Coniophora cerebella* and *Polystictus versicolor* and by the mold fungi *Aspergillus niger* and *Trichoderma viride*. The specimens were placed on biomalt nutrient agar glass plates covered with the wood-destroying fungi, and incubated at 22° C. After 16 weeks the extent of fungus spread on the specimens was assessed. The experiments with the mold fungi were carried out analogously; however, the duration was only 14 days here, as the untreated specimens were completely covered with fungus after this length of time.

| Specimen fungicide added | Extent of fungus spread on wood after 16 weeks | |
|---|---|---|
| | Coniophora cerebella | Polystictus versicolor |
| 7.5% boric acid/propylene oxide | 0 | 0 |
| 2% boric acid (comparative agent) | 2 | 1 |
| none (untreated) | 3 | 3 |

| Specimen; fungicide added | Extent of fungus spread after 14 days | |
|---|---|---|
| | Aspergillus niger | Trichoderma viride |
| 7.5% boric acid/propylene oxide | 0 | 0 |
| 2% boric acid (comparative agent) | 1 | 2 |
| none (untreated) | 3 | 3 |

0 no fungus on specimen
1 sides of specimen covered with fungus
2 specimen covered to a considerable extent with fungus
3 specimen completely covered with fungus

We claim:
1. A process for protecting wood against ligniperdous insects, termites, ligniperdous fungi, soft rot and mold fungi, which comprises bringing into contact with the wood an effective amount of wood preservative compounds effective against ligniperdous insects, termites, ligniperdous fungi, soft rot and mold fungi, said compounds being o-boric acid/propylene oxide adducts having a molar ratio of said acid to said propylene oxide in the range of 1:1 to 1:5, respectively, said adducts being formed by reacting said o-boric acid and propylene oxide either in an aprotic solvent at 100° to 160° C. in the absence of a catalyst or at 70° to 120° C. in a closed vessel in an aprotic solvent and in the presence of a catalytic amount of a base or a Lewis acid at a pressure of said propylene oxide of 4 to 9 bars, and thereafter distilling off said solvent.

2. A process as claimed in claim 1 wherein said adducts embody compounds having the formulae

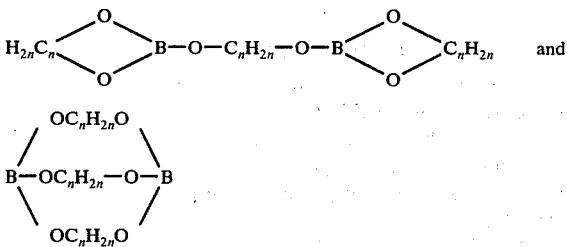

wherein $n$ denotes 3.

3. A process as claimed in claim 1 wherein said molar ratio is in the range of 1:3 to 1:4.

4. A process as claimed in claim 1 wherein the wood is coated with a liquid containing a fungicidally effective amount of said adducts.

5. A process as claimed in claim 1 wherein the wood is wood chips, and said adducts are brought into contact with said wood chips by bonding said chips with a wood glue containing an effective amount of said adducts.

* * * * *